(12) United States Patent
Koch et al.

(10) Patent No.: US 6,998,484 B2
(45) Date of Patent: Feb. 14, 2006

(54) SYNTHESIS OF PURINE LOCKED NUCLEIC ACID ANALOGUES

(75) Inventors: Troels Koch, Copenhagen S (DK); Flemming Ressig Jensen, Copenhagen Ø (DK)

(73) Assignee: Santaris Pharma A/S (DK)

( * ) Notice: Subject to any disclaimer, the term of this patent is extended or adjusted under 35 U.S.C. 154(b) by 0 days.

(21) Appl. No.: 09/971,364

(22) Filed: Oct. 4, 2001

(65) Prior Publication Data

US 2002/0086998 A1 Jul. 4, 2002

Related U.S. Application Data

(60) Provisional application No. 60/239,540, filed on Oct. 10, 2000.

(51) Int. Cl.
*C07D 473/18* (2006.01)
*C07D 473/40* (2006.01)
*C07D 473/16* (2006.01)
*C07D 473/22* (2006.01)

(52) U.S. Cl. .................. 544/276; 544/268; 544/271; 544/272; 544/229

(58) Field of Classification Search ............... 544/276, 544/277, 268, 271, 272, 229
See application file for complete search history.

(56) References Cited

U.S. PATENT DOCUMENTS 6,268,490 B1 * 7/2001 Imanishi et al. ........... 536/23.1

2004/0014959 A1 * 1/2004 Sorensen et al. ........... 544/276

FOREIGN PATENT DOCUMENTS

| EP | 1 013 661 A1 | 6/2000 |
| WO | WO 99/14226 | 3/1999 |
| WO | WO 00/47599 | 8/2000 |
| WO | WO 00/56746 | 9/2000 |

OTHER PUBLICATIONS

The Academic Press Dictionary of Science and Technology definition for alkyl.*
Hawley's Condensed Chemical Dictionary, 13th edition (1977) p. 34.*

(Continued)

*Primary Examiner*—Mark L. Berch
(74) *Attorney, Agent, or Firm*—Peter F. Corless; Christine C. O'Day; Edwards & Angell, LLP (57) ABSTRACT

The present invention relates to a new method for the synthesis of purine LNA (Locked Nucleic Acid) analogues which provides a higher overall yield. The method comprising a regioselective 9-N purine glycosylation reaction followed by a one-pot nucleophilic aromatic substitution reaction of the 6-substituent in the purine ring and simultaneous nucleophile-induced intramolecular ring closure of the C-branched carbohydrate to form novel purine LNA analogues. The novel strategy is illustrated by the synthesis of the novel compound (1S,3R,4R,7S)-7-benzyloxy-1-methanesulfonylmethyl-3-(guanin-9-yl)-2,5-dioxabicyclo[2.2.1]heptane which is easily converted into (1S,3R,4R,7S)-7-hydroxy-1-hydroxymethyl-3-((2-N-isobutyrylguanin-9-yl)-2,5-dioxabicyclo[2.2.1]heptane after isobutyryl protection of the 2-amino purine group and subsequent substitution of 1-methanesulfonyl with benzoate, debenzoylation and debenzylation.

51 Claims, 2 Drawing Sheets

Overall Synthesis

OTHER PUBLICATIONS

Encarta® World English Dictionary definition for alkyl.*

Hackh's Chemical Dictionary, 3rd edition p. 33 (1944).*

On–line Medical Dictionary definition for alkyl http://cancerweb.ncl.ac.uk/cgi–bin/omd?query=alkyl&action=Search+OMD (downloaded from the Internet Sep. 4, 2002).*

Abushanab, et al., J. Med. Chem. 1989, 32, 76–79.

P. Scheiner et al., *Nucleosides & Nucleotides*, 8(8):1441–1451 (1989).

S. Singh et al., *Chem. Commun.*, pp. 455–456 (1998).

A. Koshkin et al., *Tetrahedron,* 54:3607–3630 (1998).

C. Lomholt et al., *"Simplified and Efficient Synthesis of LNA–Monomers Based on a Novel Sugar Coupling Intermediate"* Sep. 10–14, 2000, XIV International Rountable: Nucleotides and Their Biological Applications, (San Francisco, CA).

* cited by examiner

SYNTHESIS OF PURINE LOCKED NUCLEIC ACID ANALOGUES

CROSS-REFERENCE TO RELATED APPLICATIONS

The present application claims the benefit of U.S. Provisional Patent Application No. 60/239,540 filed on 10 Oct. 2000, the disclosure of which is incorporated herein by reference.

FIELD OF THE INVENTION

The present invention relates to a new strategy for the synthesis of purine LNA (Locked Nucleic Acid) analogues which provides higher overall yields, and thus more cost efficient than previously known methods for the synthesis of purine LNA analogues.

BACKGROUND OF THE INVENTION

Synthesis of purine LNA (Locked Nucleic Acid) monomers were first reported by Wengel et al. (Singh, S. K.; Nielsen, P., Koshkin, A. A. and Wengel, J., Chem. Commun., 1998, 455; Koshkin, A. A.; Singh, S. K.; Nielsen, P.; Rajwanshi, V. K.; Kumar, R.; Meldgaard, M.; Olsen, C. E. and Wengel, J., Tetrahedron, 1998, 54, 3607). Using a convergent strategy the two purine LNA monomers (1S,3R, 4R,7S)-7-hydroxy-1-hydroxymethyl-(2-N-isobutyrylguanine-9-yl and 6-N-benzoyladenin-9-yl)-2,5-dioxabicyclo[2.2.1]heptane were synthesized in 5 steps from the key intermediate, 4-C-acetoxymethyl-1,2-di-O-acetyl-3, 5-di-O-benzyl-D-ribofuranose. Glycosylation of the key intermediate with silylated 2-N-isobutyrylguanine and 6-N-benzoyladenin afforded the 4'-C-acetoxymethyl guanine and adenine nucleosides, respectively, which upon deacetylation and monotosylation followed by base-induced ring closure, afforded the corresponding 2'-O,4'-C-methylene bicyclonucleosides. Final debenzylation afforded (1S,3R,4R,7S)-7-hydroxy-1-hydroxymethyl-(2-N-isobutyrylguanine-9-yl and 6-N-benzoyladenin-9-yl)-2,5-dioxabicyclo[2.2.1]heptane in 16% and 14% overall yields (calculated from the key intermediate), respectively. The low overall yields are primarily due to the glycosylation reactions which afford isomeric mixtures of the nucleoside analogues in ≈50% yields and the subsequent intramolecular ring closure of the C-branched carbohydrate which processed in less than 44% yield. Analogous synthetic procedures were applied for the synthesis of the thymine, uracil and 4-N-benzoylcytosine LNA nucleoside analogues.

An analogous convergent synthesis of (1S,3R,4R,7S)-7-hydroxy-1-hydroxymethyl-3-(2-N-isobutyrylguanin-9-yl and adenin-9-yl)-2,5-dioxabicyclo[2.2.1]heptane has been reported by Pfundheller, H. M. et al (Lomholt, C., Koshkin, A. A., Fensholdt, J., Meldgaard, M., and Pfundheller, H. M., poster presented at XIV International Roundtable; Nucleoside and Nucleotides and Their Biological Applications, Sep. 10–14, 2000; San Francisco, USA). Starting from the key intermediate 1,2-di-O-acetyl-3-O-benzyl-4-C-methanesulfonylmethyl-5-O-methanesulfonyl-D-ribofuranose the purine LNA monomers were obtained in 50% overall yields. This strategy, however, still suffer from the drawback of formation of isomeric mixtures in the glycosylation reaction requiring separation by chromatographic methods.

Characteristic properties of the previously known strategies discussed above are relatively low overall yields, many synthetic steps and the need of chromatographic methods for the separation of isomeric mixtures. Thus, there is a great need for development of a more efficient synthesis strategy for purine LNA analogues that will result in an improvement of the overall yield and a reduction in the production costs.

SUMMARY OF THE INVENTION

The present invention provides a novel strategy for the synthesis of purine LNA analogues comprising a regioselective 9-N purine glycosylation reaction followed by a one-pot nucleophilic aromatic substitution reaction of the 6-substituent in the purine ring and simultaneous nucleophile-induced intramolecular ring closure of the C-branched carbohydrate to form novel purine LNA analogues. The novel strategy is demonstrated by the synthesis of the novel compound (1S,3R,4R,7S)-7-benzyloxy-1-methanesulfonylmethyl-3-(guanin-9-yl)-2,5-dioxabicyclo[2.2.1]heptane which is easily converted into (1S,3R,4R, 7S)-7-hydroxy-1-hydroxymethyl-3-((2-N-isobutyrylguanin-9-yl)-2,5-dioxabicyclo[2.2.1]heptane after isobutyryl protection of the 2-amino purine group and subsequent substitution of 1-methanesulfonyl with benzoate, debenzoylation and debenzylation. The novel strategy can easily be extended to the synthesis of purine LNAs containing other 6-substituted analogues and can be further extended to other heteroatoms than oxygen in the bicycle, such as nitrogen and sulphur.

The present invention relates to a method for the synthesis of novel purine LNA analogues of the general formula I wherein the two geminal substituents $J^1$ and $J^2$ when taken together represent oxo or thiono, and when taken separately one of them represents $OR^9$, $NR^{10}R^{11}$, or $SR^{12}$, and the other together with $J^3$ represents a double bond; when $J^1$ and $J^2$ represent oxo or thiono, $J^3$ represents hydrogen;
W is selected from $NR^1R^2$, $OR^3$ and $SR^4$;
$A^1$, $A^2$, $A^3$, and $A^4$ are independently selected from —O—, —S— and —$NR^{13}$—, where $R^{13}$ is selected from hydrogen, optionally substituted $C_{1-6}$-alkyl and optionally substituted ($C_{1-6}$-alkyl)carbonyl;
each of the substituents $R^1$, $R^2$, $R^3$, $R^4$, $R^9$, $R^{10}$, $R^{11}$, and $R^{12}$ are independently selected from hydrogen, optionally substituted $C_{1-12}$-alkyl, optionally substituted $C_{2-12}$-alkenyl, optionally substituted $C_{2-12}$-alkynyl, optionally substituted aryl, optionally substituted aryl($C_{1-6}$-alkyl), optionally substituted arylcarbonyl, optionally substituted aryl($C_{1-6}$alkyl) carbonyl, optionally substituted $C_{1-12}$-alkyl carbonyl, optionally substituted $C_{2-12}$-alkenyl carbonyl, optionally substituted $C_{2-12}$-alkynyl carbonyl, optionally substituted arylsulfonyl, optionally substituted $C_{1-12}$-alkylsulfonyl, optionally substituted $C_{2-12}$-alkenylsulfonyl, optionally substituted $C_{2-12}$-alkynylsulfonyl, $C_{1-12}$-alkoxycarbonyl, formyl, tetrahydropyran-2-yl, optionally substituted heteroaryl, optionally substituted heteroarylcarbonyl, carbamoyl, and "active/functional" groups of the general form M-K where M is the "active/functional" part of the group in question selected from the group consisting of DNA intercalators, photochemically active groups, thermochemically active groups, chelating groups, reporter groups, and ligands and K is a spacer through which the "active/functional" part is attached to the purine ring, and where K is an optional spacer comprising 1–50 atoms;

$R^5$ is selected from optionally substituted alkylsulfonyl, optionally substituted arylsulfonyl, optionally substituted aryl($C_{1-6}$alkyl), optionally substituted arylcarbonyl and tri(alkyl/aryl)silyl;

$R^6$ is selected from optionally substituted aryl($C_{1-6}$-alkyl), optionally substituted tetrahydropyran-2-yl, optionally substituted arylcarbonyl, optionally substituted aryl and tri(alkyl/aryl)silyl;

taken together $R^5$ and $R^6$ may also represent dialkyldisiloxanylidene; and n is an integer from 1 to 3;

said method comprising the following step:

treatment of a compound (hereinafter termed "key intermediate") of the general formula II:

II wherein $A^1, A^2, A^3, A^4, R^5, R^6, R^{13}$, W and n are as defined above;

$A^5$ is selected from —O—, —S— and —$NR^{13}$—;

$R^7$ is selected from optionally substituted alkylsulfonyl, optionally substituted arylsulfonyl, optionally substituted aryl($C_{1-6}$alkyl), optionally substituted arylcarbonyl and tri(alkyl/aryl)silyl;

$R^8$ is selected from hydrogen, optionally substituted ($C_{1-6}$-alkyl)carbonyl, optionally substituted arylcarbonyl, tri(alkyl/aryl)silyl, and fluorenyl($C_{1-6}$-alkyl)oxycarbonyl; and

X is selected from halogen, CN, optionally substituted sulfonyl and optionally substituted arylsulfonyl;

with a nucleophilic reagent.

The present invention also relates to compounds of the general formula I as defined above.

The present invention furthermore relates to a method for the synthesis of the key intermediate of the general formula II, said method comprising the following step:

coupling of the compound (hereinafter termed the "starting material") of the general formula III:

III wherein $A^1, A^2, A^3, A^4, A^5, R^5, R^6, R^7, R^8$ and n are as defined above; and $R^{14}$ is selected from optionally substituted ($C_{1-6}$-alkyl) carbonyloxy, optionally substituted $C_{1-6}$-alkoxy, halogen, optionally substituted arylthio, optionally substituted $C_{1-6}$-alkylthio, and optionally substituted aryloxy;

with a purine of the general formula IV:

IV wherein X and W are as defined above;

in a glycosylation reaction.

The present invention furthermore relates to novel compounds of the general formula II as defined above.

The main advantages of the present invention comprise the following:

One-pot nucleophilic substitution reaction of purine 6-halide (or similar) and simultaneous nucleophile-induced intramolecular ring closure of the C-branched carbohydrate to form novel purine LNA analogues.

Convenient access to purine LNAs analogues comprising a variety of substituents in the aromatic 6-position.

Convenient access to purine LNA monomers which are amenable to oligomerization.

Regioselective 9-N purine glycosylation of the starting material of the general formula III eliminating the need of chromatographic separation of nucleic acid isomers.

DETAILED DESCRIPTION OF THE INVENTION

Figure 1:
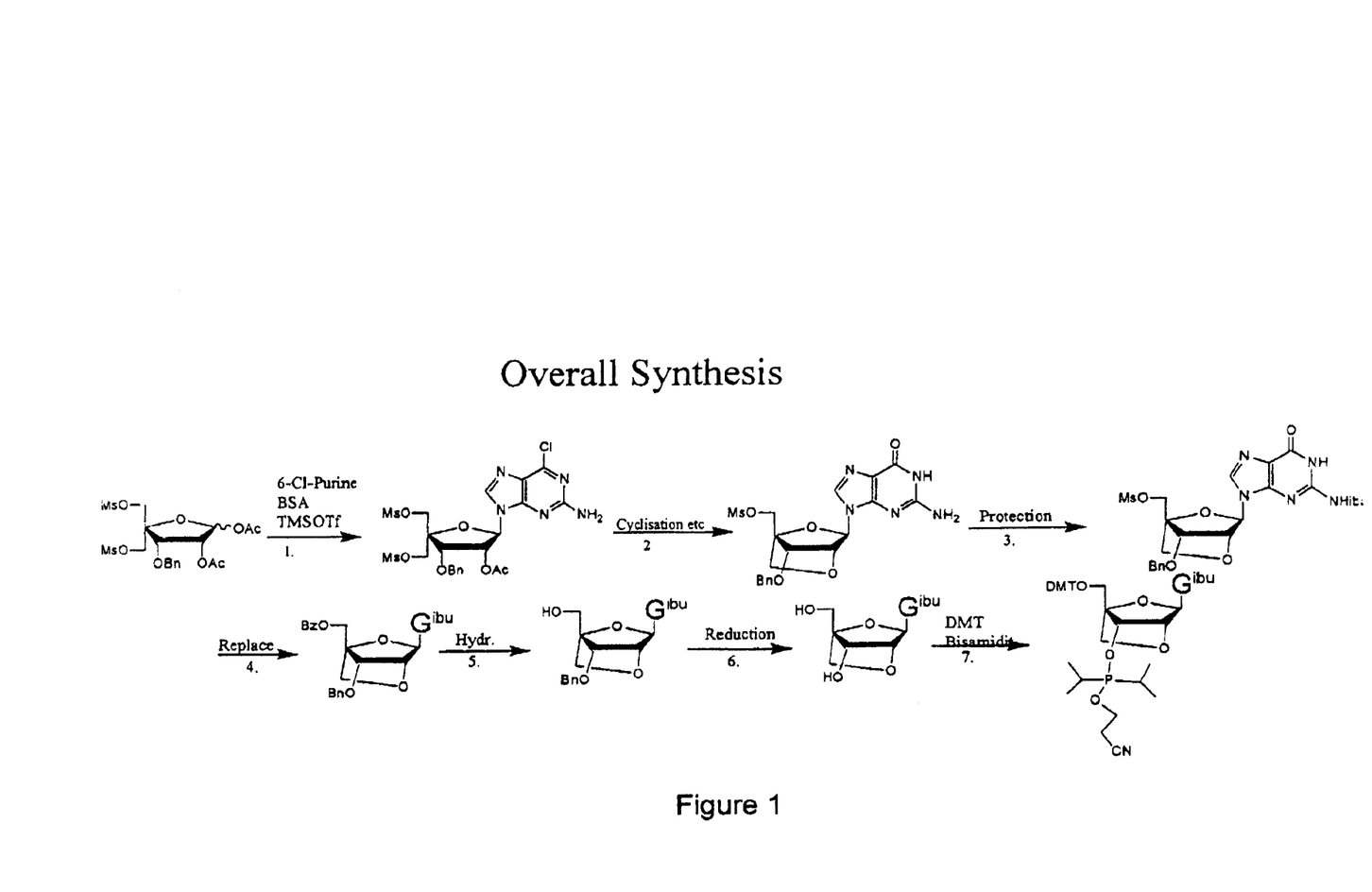
FIG. 1 illustrates an overall synthesis of G-LNA utilising the invention.
Figure 2:
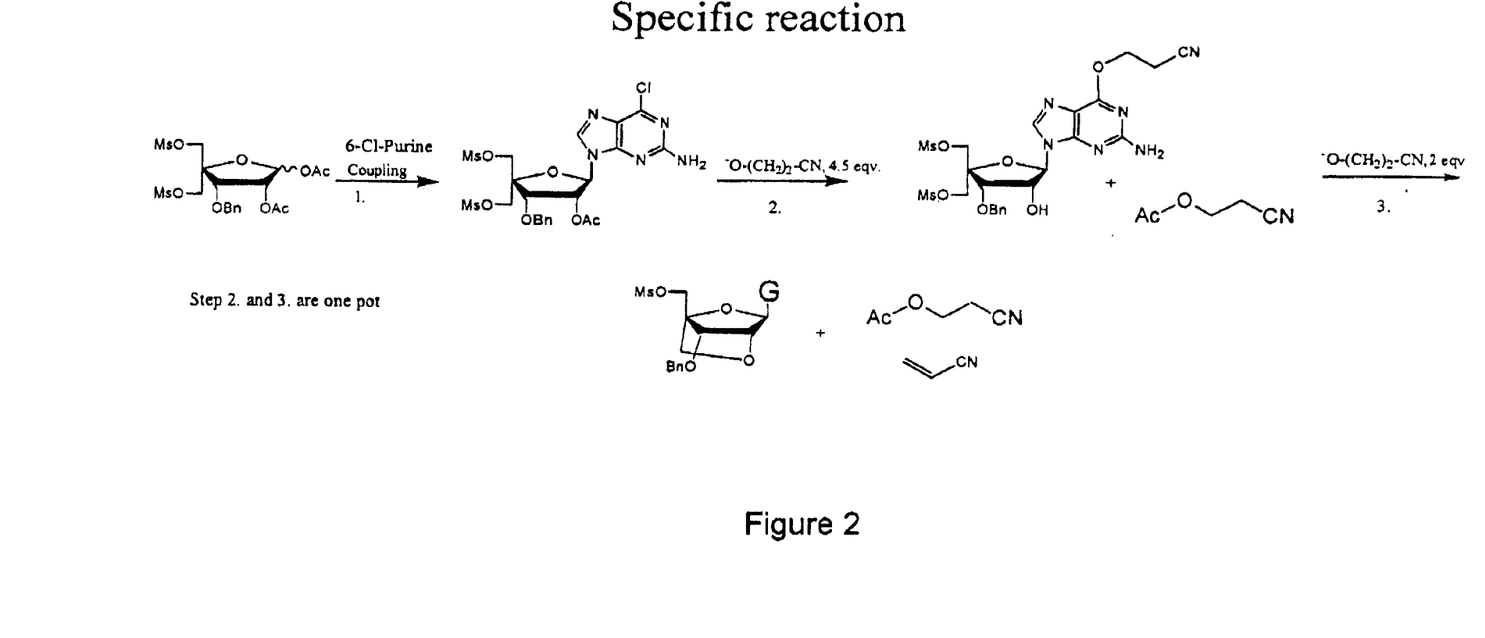
FIG. 2 illustrates the novel strategy according to the invention comprising: regioselective 9-N purine glycosylation reaction followed by a one-pot nucleophilic aromatic substitution reaction of the 6-chloro in the purine ring and nucleophile-induced intramolecular ring closure of the C-branched carbohydrate to form guanine-9-yl LNA.

In an attempt to improve the synthesis of purine LNA analogues, a novel strategy for regioselective 9-N purine glycosylation and intramolecular ring-closure has been developed. Using this novel synthesis strategy, (1S,3R,4R,7S)-7-benzyloxy-1-methanesulfonylmethyl-3-(guanin-9-yl)-2,5-dioxabicyclo[2.2.1]heptane was synthesised in high yield in only two steps from 1,2-di-O-acetyl-3-O-benzyl-4-C-methanesulfonylmethyl-5-O-methanesulfonyl-D-ribofuranose. Regioselective glycosylation of 1,2-di-O-acetyl-3-O-benzyl-4-C-methanesulfonylmethyl-5-O-methanesulfonyl-D-ribofuranose was performed using 2-amino-6-chloropurine as the heterocyclic base in a "one pot" Vorbrüggen glycosylation reaction affording the 9-N purine nucleic acid isomer as the only product. The fact that the glycosylation reaction proceed regioselective in the favour of the 9-N purine nucleic acid isomer and that the subsequent nucleophilic substitution of 6-chloro purine can be performed in a one-pot reaction together with the nucleophile-induced ring closure of the C-branched carbohydrate makes this novel synthesis more convenient and much more cost efficient than previously known strategies. This novel synthesis strategy furthermore provides convenient access to purine LNAs analogues comprising a variety of substituents in the 6-position as well as purine LNA monomers which are amenable to oligomerization.

The present invention relates to a method for the synthesis of purine LNA analogues of the general formula I as defined above:

The method of the invention comprises treatment of the key intermediate of the general formula II as defined above:

with a nucleophilic reagent.

In a preferred embodiment of the invention the nucleophilic reagent is selected from optionally substituted hydroxy($C_{1-6}$-alkane), optionally substituted phenol, optionally substituted hydroxy($C_{1-6}$-alkyl)benzene, $NH_3$, optionally substituted amino($C_{1-6}$-alkane), optionally substituted aniline, optionally substituted amino($C_{1-6}$-alkyl)benzene, optionally substituted thio($C_{1-6}$-alkane), optionally substituted benzenethiol, optionally substituted thio($C_{1-6}$-alkyl)benzene, M-K—OH, M-K—$NH_2$ and M-K—SH (e.g. where M is a flurophor (such as flourescein, pyrene, anthracene, etc.), biotin, anthraqinonyl, etc. and K is —$(CH_2)_n$— such as described below). It is presently believed that 3-hydroxypropionitrile, $NH_3$, 3-mercaptopropionitrile, benzyl alcohol, 2-hydroxy-ethylbenzene, 2-hydroxy-1-nitroethane, and benzylamine, in particular 3-hydroxypropionitrile, are the most suitable nucleophiles.

The molar ratio between compound II and the nucleophilic reagent is typically in the range of 1:2 to 1:10, preferably 1:2–1:8, more preferably 1:2–1:6.

Based on the present invention, it should be clear to a person skilled in the art that some of the nucleophilic reagents when used in excess can bring about an additional elimination reaction of the initially formed substitution product affording the 6-oxo-and 6-thio purine LNA analogues. A feature of these nucleophilic reagents is that they comprise an acidic α-hydrogen which can participate in a β-elimination reaction such as 3-hydroxypropionitrile, 3-mercaptopropionitrile, 2-hydroxy-ethylbenzene, 2-hydroxy-1-nitroethane.

The treatment of compound II with the nucleophilic reagent is typically performed at −30° C. to 100° C., such as −20° C. to 60° C.

It should be understood that the treatment of compound II with the nucleophilic reagent may be carried out in the presence of a non-nucleophilic strong base, such as NaH, LiH, lithium diisopropylamide, and lithium tert-butoxide. The presence of a non-nucleophilic strong base will generate the desired nucleophile. In a preferred embodiment of the invention, the treatment is performed in the presence of NaH or LiH, preferably NaH.

For a person skilled in the art, it should also be clear that the treatment of compound II with the nucleophilic reagent typically is carried out in the presence of a solvent, such as tetrahydrofuran, toluene, xylene, benzene, diethyl ether, acetonitril, triethylamine, N,N-dimethylformamide, dimethylsulfoxide, dichloromethane, and 1,2-dichloroethane, preferably tetrahydrofuran.

In a preferred embodiment of the invention each of the substituents $A^1$, $A^2$, $A^3$, $A^4$ and $A^5$ represent —O—. In the embodiment where one or more of the substituents $A^1$, $A^2$, $A^3$, $A^4$ and $A^5$ represent —$NR^{13}$—, $R^{13}$ preferably represents hydrogen or methyl, most preferably hydrogen.

In a preferred embodiment of the invention, W represents OH, SH or $NH_2$, preferably $NH_2$.

In a preferred embodiment of the invention the substituents $J^1$ and $J^2$ together represent oxo or thiono, preferably oxo, and $J^3$ represent hydrogen.

In a further embodiment of the invention $J^1$ represents $OR^9$, $NR^{10}R^{11}$, or $SR^{12}$, and $J^2$ together with $J^3$ represents a double bond.

In a preferred embodiment of the invention X is selected from chloro, fluoro, bromo, iodo, CN, methanesulfonyl, α-toluenesulfonyl, preferably chloro.

n is an integer from 1 to 3, such as 1, 2 or 3, preferably n is 1.

Each of the substituents $R^1$, $R^2$, $R^3$, $R^4$, $R^9$, $R^{10}$, $R^{11}$, and $R^{12}$ are preferably independently selected from hydrogen, methyl, trifluoromethyl, ethyl, propyl, iso-propryl, butyl, t-butyl, pentyl, cyclopentyl, hexyl, cyclohexyl, phenyl, benzyl, phenylethyl, ortho-, meta-, and para-methylbenzyl, 2-chlorobenzyl, 4-phenylbenzyl, 2-cyanoethyl, and "active/functional" groups where M designates psoralens, ethidium bromide, acridine, anthraquinone, biotin, rhodamine or fluorescein and K designates polyethylene glycol, polymethylene, etc.

In one embodiment of the present invention, K designates a single bond so that the "active/functional" part of the group in question is attached directly to the purine ring.

In a preferred embodiment of the invention, each of the substituents $R^5$ and $R^7$ independently represent methanesulfonyl, trifluoromethanesulfonyl, ethanesulfonyl, 2,2,2-trifluoroethanesulfonyl, propanesulfonyl, iso-propanesulfonyl, butanesulfonyl, nonafluorobutanesulfonyl, pentanesulfonyl, cyclopentanesulfonyl, hexanesulfonyl, cyclohexanesulfonyl, α-toluenesulfonyl, 2-chloro-α-toluenesulfonyl, ortho-, meta-, para-toluenesulfonyl, benzenesulfonyl, ortho-, meta-, para-bromobenzenesulfonyl, ortho-, meta-, para-nitrobenzenesulfonyl, trimethylsilyl, triethylsilyl, triisopropylsilyl, dimethylisopropylsilyl, diethylisopropylsilyl, dimethylthexylisopropylsilyl, tert-butyldimethylsilyl, tert-butyldiphenylsilyl, tribenzylsilyl, tri-para-xylylsilyl, triphenylsilyl, diphenylmethylsilyl, di-tert-butylmethylsilyl, tris(trimethylsilyl)silyl, tert-butylmethoxyphenylsilyl, tert-butoxydiphenylsilyl, benzyl, ortho-, meta-, para-methylbenzyl, 2-chlorobenzyl and 4-phenylbenzyl.

In a further embodiment of the invention, $R^5$ and $R^7$ represent methanesulfonyl, trifluoromethanesulfonyl, ethanesulfonyl, 2,2,2-trifluoroethanesulfonyl, butanesulfonyl, nonafluorobutanesulfonyl, α-toluenesulfonyl, para-toluenesulfonyl, benzenesulfonyl, para-bromobenzenesulfonyl, para-nitrobenzenesulfonyl, trimethylsilyl, tert-butyldimethylsilyl, tert-butyldiphenylsilyl, tert-butylmethoxyphenylsilyl and tert-butoxydiphenylsilyl, preferably methanesulfonyl, trifluoromethanesulfonyl, para-toluenesulfonyl and para-bromobenzenesulfonyl, more preferably methanesulfonyl, and para-toluenesulfonyl, even more preferably methanesulfonyl.

In an especially preferred embodiment of the invention, $R^5$ and $R^7$ are identical and are selected from methanesulfonyl, trifluoromethanesulfonyl, ethanesulfonyl, 2,2,2-trifluoroethanesulfonyl, butanesulfonyl, nonafluorobutanesulfonyl, α-toluenesulfonyl, para-toluenesulfonyl, benzenesulfonyl, para-bromobenzenesulfonyl, and para-nitrobenzene-sulfonyl, preferably methanesulfonyl, trifluoromethanesulfonyl, para-toluenesulfonyl and para-bromobenzenesulfonyl, more preferably methanesulfonyl, and para-toluenesulfonyl, even more preferably methanesulfonyl.

Some preferred embodiments of $R^6$ comprise benzyl, ortho-, meta-, para-methylbenzyl, 2-chlorobenzyl, 4-phenylbenzyl, tetrahydropyran-2-yl, benzoyl, phenyl, trimethylsilyl, triethylsilyl, triisopropylsilyl, dimethylisopropylsilyl, diethylisopropylsilyl, dimethylthexyl, isopropylsilyl, tert-butyldimethylsilyl, tert-butyldiphenylsilyl, tribenzylsilyl, tri-para-xylylsilyl, triphenylsilyl, diphenylmethylsilyl, di-tert-butylmethylsilyl, tris(trimethylsilyl)silyl, tert-butylmethoxyphenylsilyl, tert-butoxydiphenylsilyl among which benzyl is preferred.

In one embodiment of the invention $R^5$ and $R^6$ together represent di-tert-butylsilylene, 1,3-(1,1,3,3-tetraisopropyl) disiloxanylidene or 1,3-(1,1,3,3-tetra-tert-butoxy) disiloxanylidene.

In a preferred embodiment of the invention $R^8$ is selected from hydrogen, optionally substituted alkylcarbonyl (e.g. acetyl and trifluoroacetyl), optionally substituted arylcarbonyl (e.g. benzoyl and m-trifluoromethylbenzoyl), tert-butyldimethylsilyl, tert-butyldiphenylsilyl, and 9-fluorenylmethyloxycarbonyl, with the proviso that when $A^4$ represent —NR$^{13}$—, then $R^8$ is selected from trifluoroacetyl and 9-fluorenylmethyloxy-carbonyl.

In a preferred embodiment of the invention $R^8$ is selected from acetyl, benzoyl and m-trifluoromethylbenzoyl, preferably acetyl.

In one embodiment of the invention $R^6$ represents benzyl, $R^5$ and $R^7$ both represent methanesulfonyl, and $R^8$ represents acetyl.

In an especially preferred embodiment of the invention, $A^1$, $A^2$, $A^3$, $A^4$ and $A^5$ all represent oxygen, X is chloro, W is $NH_2$, both of the substituents $R^5$ and $R^7$ are methanesulfonyl, $R^6$ represents benzyl, $R^8$ represent acetyl and n is 1.

The present invention also relates to the compound of the general formula I as defined above, with the proviso that $R^1$ is not hydrogen and $R^2$ is not isobutyryl or vice versa when $A^1$, $A^2$, $A^3$ and $A^4$ all represent oxygen, $R^5$ is methanesulfonyl, $R^6$ is benzyl and n is 1.

The present invention furthermore relates to a method for the synthesis of the key intermediate of the general formula II, said method comprising the following step:
coupling of the starting material of the general formula III:

III wherein $A^1$, $A^2$, $A^3$, $A^4$, $A^6$, $R^5$, $R^6$, $R^7$, $R^8$ and n are as defined above; and $R^{14}$ is selected from optionally substituted ($C_{1-6}$-alkyl) carbonyloxy, optionally substituted $C_{1-6}$-alkoxy, halogen, optionally substituted arylthio, optionally substituted $C_{1-6}$-alkylthio, and optionally substituted aryloxy, such as acetyloxy, methoxy, ethoxy, chloride, fluoride, bromide or iodide, or $SC_6H_5$.
with a purine of the general formula IV:

IV wherein X and W are as defined above;
in a glycosylation reaction.

In a preferred embodiment of the invention the glycosylation reaction is performed according to the Vorbrüggen glycosylation method involving the reaction of the starting material III with silylated purine in the presence of a Lewis acid.

In one embodiment of the invention, the glycosylation reaction is performed as a "one-pot" Vorbrüggen glycosylation reaction involving the coupling of the starting material III with the purine. The reaction can be facilitated in the presence of a silylating agent, such as N,O-bis(trimethylsilyl)acetamide (BSA) and 1,1,1,3,3,3-hexamethyldisilazane (HMDS), and/or a Lewis acid such as tin(IV)chloride and trimethylsilyl trifluoromethansulfonate (TMS-triflate).

In a preferred embodiment of the invention the silylating agent is N,O-bis(trimethylsilyl)acetamide and the Lewis acid is trimethylsilyl trifluoromethansulfonate.

In a further preferred embodiment of the invention $R^8$ is selected from acetyl, benzoyl and m-trifluoromethylbenzoyl, preferably acetyl, and $R^{14}$ is selected from acetyloxy, methoxy, ethoxy, chloride, fluroride, bromide, iodide and $SC_6H_5$, preferably acetyloxy and methoxy, even more preferably acetyloxy.

In the most preferred embodiment of the invention $A^1$, $A^2$, $A^3$, $A^4$ and $A^5$ all represent oxygen, $R^6$ represents benzyl, $R^5$ and $R^7$ both represent methanesulfonyl, $R^8$ represents acetyl, and $R^{14}$ represents acetyloxy.

The present invention furthermore relates to compounds of the general formula II as defined above.
Synthesis of Purine LNA Analogues As a illustrative example of synthesis of purine LNAs using the method of the present invention (1S,3R,4R,7S)-7-benzyloxy-1-methanesulfonylmethyl-3-(2-N-isobutyrylguanin-9-yl)-2,5-dioxabicyclo[2.2.1]heptane (6) was synthesized using 1,2-di-O-acetyl-3-O-benzyl-4-C-methanesulfonylmethyl-5-O-methanesulfonyl-D-ribofuranose (3) as starting material. "One pot" glycosylation of 3 with 2-amino-6-chloropurine using N,O-bis(trimethylsilyl) acetamide (BSA) as silylating agent and trimethylsilyltriflat in 1,2-dichloroethane afforded 4. Compound 4 was used in the following step without further purification. "One pot" nucleophilic substitution of 6-chloropurine using 3-hydroxypropionitrile (4.5 equivalents) followed by nucleophile-induced ring closure afforded 5. Isobutyryl protection of the 2-amino purine group was performed by heating 5 overnight with isobutyric anhydride in the presence of N,N-dimethyl aminopyridine affording 6 in quantitative yield after aqueous work up. Substitution with benzoate, debenzoylation and debenzylation gave 9 in 3 steps. The nucleoside phosphoramidite 11 was obtained according to Koshkin et al (*Tetrahedron*, 1998, 54, 3607–3630).

Definitions

In the present context, the term "$C_{1-12}$-alkyl" means a linear or branched hydrocarbon group having 1 to 12 carbon atoms, such as methyl, ethyl, propyl, iso-propyl, butyl, tert-butyl, iso-butyl, pentyl, hexyl, and dodecyl. Analogously, the term "$C_{1-6}$-alkyl" means a linear, or branched hydrocarbon group having 1 to 6 carbon atoms, such as methyl, ethyl, propyl, iso-propyl, butyl, tert-butyl, iso-butyl, pentyl, hexyl, in particular methyl, ethyl, propyl, iso-propyl, tert-butyl, and iso-butyl.

Similarly, the term "$C_{2-12}$-alkenyl" covers linear or branched hydrocarbon groups having 2 to 12 carbon atoms and comprising one unsaturated bond. Examples of alkenyl groups are vinyl, allyl, butenyl, pentenyl, hexenyl, heptenyl, octenyl, dodecaenyl.

The term "$C_{1-12}$-cycloalkyl" means a cyclic hydrocarbon group having 1 to 12 carbon atoms, such as cyclopropyl, cyclobutyl, cyclopentyl and cyclohexyl. Analogously, the term "$C_{1-6}$-cycloalkyl" means a cyclic hydrocarbon group having 1 to 6 carbon atoms, such as cyclopentyl and cyclohexyl. Similarly, the term "$C_{2-12}$-cycloalkenyl" covers cyclic hydrocarbon groups having 2 to 12 carbon atoms and comprising one unsaturated bond.

Similarly, the term "$C_{2-12}$-alkynyl" means a linear or branched hydrocarbon group having 2 to 12 carbon atoms and comprising a triple bond. Examples hereof are ethynyl, propynyl, butynyl, octynyl, and dodecanyl.

In the present context, i.e. in connection with the terms "alkyl", "alkenyl", and "alkynyl", the term "optionally substituted" means that the group in question may be substituted one or several times, preferably 1–3 times, with group(s) selected from hydroxyl, $C_{1-6}$-alkoxy, carboxyl, $C_{1-6}$-alkoxycarbonyl, $C_{1-6}$-alkylcarbonyl, formyl, aryl, aryloxycarbonyl, arylcarbonyl, heteroaryl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, carbamido, halogen, where aryl and heteroaryl may be substituted 1–5 times, preferably 1–3 times, with $C_{1-4}$-alkyl, $C_{1-4}$-alkoxy, nitro, cyano, amino or halogen. Especially preferred examples are hydroxyl, $C_{1-6}$-alkoxy, carboxyl, aryl, heteroaryl, amino, mono- and di($C_{1-6}$-alkyl)amino, and halogen, where aryl and heteroaryl may be substituted 1–3 times with $C_{1-4}$-alkyl, $C_{1-4}$-alkoxy, nitro, cyano, amino or halogen. Aryl and heteroaryl may be substituted as specifically describe below for "optionally substituted aryl and heteroaryl".

In the present context the term "aryl" means a fully or partially aromatic carbocyclic ring or ring system, such as phenyl, naphthyl, 1,2,3,4-tetrahydronaphthyl, anthracyl, phenanthracyl, pyrenyl, benzopyrenyl, fluorenyl and xanthenyl, among which phenyl is a preferred example.

The term "heteroaryl" means a fully or partially aromatic carbocyclic ring or ring system where one or more of the carbon atoms have been replaced with heteroatoms, e.g. nitrogen (=N— or —NH), sulphur, and/or oxygen atoms. Examples of such heteroaryl groups are oxazolyl, isoxazolyl, thiazolyl, isothiazolyl, pyrrolyl, imidazolyl, pyrazolyl, pyridinyl, pyrazinyl, pyridazinyl, piperidinyl, coumaryl, furyl, quinolyl, benzothiazolyl, benzotriazolyl, benzodiazolyl, benzooxozolyl, phthalazinyl, phthalanyl, triazolyl, tetrazolyl, isoquinolyl, acridinyl, carbazolyl, dibenzazepinyl, indolyl, benzopyrazolyl, phenoxazonyl.

In the present context, i.e. in connection with the terms "aryl" and "heteroaryl", the term "optionally substituted" means that the group in question may be substituted one or several times, preferably 1–5 times, in particular 1–3 times with group(s) selected from hydroxyl (which when present in an enol system may be represented in the tautomeric keto form), $C_{1-6}$-alkyl, $C_{1-6}$-alkoxy, oxo (which may be represented in the tautomeric enol form), carboxyl, $C_{1-6}$-alkoxycarbonyl, $C_{1-6}$-alkylcarbonyl, formyl, aryl, aryloxy, aryloxycarbonyl, arylcarbonyl, heteroaryl, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkanoyloxy, sulphono, $C_{1-6}$-alkylsulphonyloxy, nitro, sulphanyl, dihalogen-$C_{1-4}$-alkyl, trihalogen-$C_{1-4}$-alkyl, halogen, where aryl and heteroaryl representing substituents may be substituted 1–3 times with $C_{1-4}$-alkyl, $C_{1-4}$-alkoxy, nitro, cyano, amino or halogen. Preferred examples are hydroxyl, $C_{1-6}$-alkyl, $C_{1-6}$-alkoxy, carboxyl, $C_{1-6}$-alkoxycarbonyl, $C_{1-6}$-alkylcarbonyl, aryl, amino, mono- and di($C_{1-6}$-alkyl)amino, and halogen, wherein aryl may be substituted 1–3 times with $C_{1-4}$-alkyl, $C_{1-4}$-alkoxy, nitro, cyano, amino or halogen.

In the present context, the term "tri(alkyl/aryl)silyl" means a silyl group substituted with 0–3 alkyl groups and/or 0–3 aryl groups, with the provision that the total number of alkyl and aryl groups is 3, selected from trimethylsilyl, dimethylphenylsilyl, diphenylmethylsilyl, isopropyldimethylsilyl, tert-butyldimethylsilyl, tert-butyldiphenylsilyl, triethylsilyl, triisopropylsilyl, diethylisopropylsilyl, dimethylthexylisopropylsilyl, tri-para-xylylsilyl, triphenylsilyl, diphenylmethylsilyl, di-tert-butylmethylsilyl, tris(trimethyl-silyl)silyl, tert-butylmethoxyphenylsilyl.

In the present context, the term "dialkyldisiloxanylidene" means siloxane substituted with 4 alkyl groups selected from 1,3-(1,1,3,3-tetraisopropyl)disiloxanylidene and 1,3-(1,1,3, 3-tetra-tert-butoxy)disiloxanylidene.

"Halogen" includes fluoro, chloro, bromo, and iodo.

When used herein, the term "DNA intercalator" means a group which can intercalate into a DNA or RNA helix, duplex or triplex. Examples of functional parts of DNA intercalators are acridines, anthracene, quinones such as anthraquinone, indole, quinoline, isoquinoline, dihydroquinones, anthracyclines, tetracyclines, methylene blue, anthracyclinone, psoralens, coumarins, ethidium-halides, dynemicin, metal complexes such as 1,10-phenanthroline-copper, tris(4,7-diphenyl-1,10-phenanthroline)ruthenium-cobalt-enediynes such as calcheamicin, porphyrins, distamycin, netropcin, viologen, daunomycin. Especially interesting examples are acridines, quinones such as anthraquinone, methylene blue, psoralens, coumarins, and ethidium-halides.

In the present context, the term "photochemically active groups" covers compounds which are able to undergo chemical reactions upon irradiation with light. Illustrative examples of functional groups hereof are quinones, especially 6-methyl-1,4-naphtoquinone, anthraquinone, naphtoquinone, and 1,4-dimethyl-anthraquinone, diazirines, aromatic azides, benzophenones, psoralens, diazo compounds, and diazirino compounds.

In the present context "thermochemically reactive group" is defined as a functional group which is able to undergo thermochemically-induced covalent bond formation with other groups. Illustrative examples of functional parts thermochemically reactive groups are carboxylic acids, carboxylic acid esters such as activated esters, carboxylic acid halides such as acid fluorides, acid chlorides, acid bromide, and acid iodides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, and boronic acid derivatives.

In the present context, the term "chelating group" means a molecule that contains more than one binding site and frequently binds to another molecule, atom or ion through more than one binding site at the same time. Examples of functional parts of chelating groups are iminodiacetic acid, nitrilotriacetic acid (NTA), ethylenediamine tetraacetic acid (EDTA), aminophosphonic acid, etc.

In the present context, the term "reporter group" means a group which is detectable either by itself or as a part of an detection series. Examples of functional parts of reporter groups are biotin, digoxigenin, fluorescent groups (groups which are able to absorb electromagnetic radiation, e.g. light or X-rays, of a certain wavelength, and which subsequently reemits the energy absorbed as radiation of longer wavelength; illustrative examples are dansyl (5-dimethylamino)-1-naphthalenesulfonyl), DOXYL (N-oxyl-4,4-dimethyloxazolidine), PROXYL (N-oxyl-2,2,5,5-tetramethylpyrrolidine), TEMPO (N-oxyl-2,2,6,6-tetramethylpiperidine), dinitrophenyl, acridines, coumarins, Cy3 and Cy5 (trademarks for Biological Detection Systems, Inc.), erytrosine, coumaric acid, umbelliferone, texas red, rhodamine, tetramethyl rhodamine, Rox, 7-nitrobenzo-2-oxa-1-diazole (NBD), pyrene, fluorescein, Europium, Ruthenium, Samarium, and other rare earth metals), radio-isotopic labels, chemiluminescence labels (labels that are detectable via the emission of light during a chemical reaction), spin labels (a free radical (e.g. substituted organic nitroxides) or other paramagnetic probes (e.g. $Cu^{2+}$, $Mg^{2+}$) bound to a biological molecule being detectable by the use of electron spin resonance spectrometry), enzymes (such as peroxidases, alkaline phosphatases, β-galactosidases, and glucose oxidases), antigens, antibodies, haptens (groups which are able to combine with an antibody, but which cannot initiate an immune response by itself, such as peptides and steroid hormones), carrier systems for cell membrane penetration such as: fatty acid residues, steroid moieties (cholesteryl), vitamin A, vitamin D, vitamin E, folic acid peptides for specific receptors, groups for mediating endocytose, epidermal growth factor (EGF), bradykinin, and platelet derived growth factor (PDGF). Especially interesting examples are biotin, fluorescein, Texas Red, rhodamine, dinitrophenyl, digoxigenin, Ruthenium, Europium, Cy5, Cy3, etc.

In the present context "ligand" means something which binds. Ligands can comprise functional groups such as: aromatic groups (such as benzene, pyridine, naphtalene, anthracene, and phenanthrene), heteroaromatic groups (such as thiophene, furan, tetrahydrofuran, pyridine, dioxane, and pyrimidine), carboxylic acids, carboxylic acid esters, carboxylic acid halides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, $C_{1-C_{20}}$ alkyl groups optionally interrupted or terminated with one or more heteroatoms such as oxygen atoms, nitrogen atoms, and/or sulphur atoms, optionally containing aromatic or mono/polyunsaturated hydrocarbons, polyoxyethylene such as polyethylene glycol, oligo/polyamides such as poly-β-alanine, polyglycine, polylysine, peptides, oligo/polysaccharides, oligo/polyphosphates, toxins, antibiotics, cell poisons, and steroids, and also "affinity ligands", i.e. functional groups or biomolecules that have a specific affinity for sites on particular proteins, antibodies, poly- and oligosaccharides, and other biomolecules.

In the present context, the term "spacer" means a thermochemically and photochemically non-active distance-making group and is used to join two or more different moieties of the types defined above. Spacers are selected on the basis of a variety of characteristics including their hydrophobicity, hydrophilicity, molecular flexibility and length (e.g. see Hermanson et. al., "Immobilised Affinity Ligand Techniques", Academic Press, San Diego, Calif. (1992), p. 137-ff). Generally, the length of the spacers is less than or about 400 Å, in some applications preferably less than 100 Å. The spacer, thus, comprises a chain of carbon atoms optionally interrupted or terminated with one or more heteroatoms, such as oxygen atoms, nitrogen atoms, and/or sulphur atoms. Thus, the spacer K may comprise one or more amide, ester, amino, ether, and/or thioether functionalities, and optionally aromatic or mono/polyunsaturated hydrocarbons, polyoxyethylene such as polyethylene glycol, oligo/polyamides such as poly-β-alanine, polyglycine, polylysine, and peptides in general, oligosaccharides, oligo/polyphosphates. Moreover the spacer may consist of combined units thereof. In particularly interesting embodiments, the spacer includes a chemically cleavable group. Examples of such chemically cleavable groups include disulphide groups cleavable under reductive conditions, peptide fragments cleavable by peptidases, or selenides cleavable under oxidative conditions, etc.

In the present context, the term "nucleoside" means a glycoside of a heterocyclic base. The term "nucleoside" is used broadly as to include non-naturally occurring nucleosides, naturally occurring nucleosides as well as other nucleoside analogues. Illustrative examples of nucleosides are ribonucleosides comprising a ribose moiety as well as deoxyribonuclesides comprising a deoxyribose moiety. With respect to the bases of such nucleosides, it should be understood that this may be any of the naturally occurring bases, e.g. adenine, guanine, cytosine, thymine, and uracil, as well as any modified variants thereof or any possible unnatural bases.

The following examples were performed in order to illustrate the invention.

EXPERIMENTAL

EXAMPLE 1

3-O-benzyl-4-C-methanesulfonoxymethyl-5-methanesulfonyl-1,2-O-isopropylidene-β-D-ribofuranose (2)

A solution of 3-O-benzyl-4-C-hydroxymethyl-1,2-O-isopropylidene- -D-ribofuranose (1, 11.1 g, 40 mmol) (Youssefyeh, R. D.; Verheyden, J. P. H.; Moffatt, J. G., J. Org. Chem. 1979, 44, 1301) in dry pyridine (30 mL) was cooled in an ice-bath. Methanesulfonyl chloride (8.3 mL, 108 mmol) was then added under stirring. The mixture was allowed to warm up to room temperature and stirred for 1 hr. Ether (200 mL) was added and the solution was washed with water (3×200 mL). Organic layer was dried over $Na_2SO_4$ and concentrated under reduced pressure to give 16.4 g (98%) of compound (2) as slightly yellow solid.

EXAMPLE 2

1,2-O-acetyl-3-O-benzyl-4-C(methanesulfonyloxymethyl)-5-O-methanesulfonyl oxymethyl-)-β-D-ribofuranose (3)

1,2-O-isopropylidene-3-O-benzyl-4-C-methanesulfonyloxymethyl-5-O-methanesulfonyloxymethyl-β-D-ribofuranose (2, 20 g, 43 mmol) is dissolved in acetic acid (175 ml), acetic anhydride (28 ml) is added and finally 320 µl concentrated sulphuric acid. The solution is stirred over night. The solution is then evaporated to half volume at a water bath temperature at 35° C. Then water (300 ml) is added. The formed emulsion is extracted 3 times with ether (150 ml) and twice with DCM (at this point an emulsion is formed). The combined organic phases are washed twice with water and saturated $HCO_3^-$ (intense $CO_2$ evolution). The organic phase is evaporated to a syrup, redissolved in DCM (200 ml) and residual acetic anhydride is quenched by vigorously agitation in a two phase system of DCM and saturated $HCO_3^-$ (150 ml). Additional $HCO_3^-$ (solid) may be added if the aqueous phase turns acidic. After 3 h no more gas is evolved, the aqueous phase is still basic (pH=8), the phases are separated and the aqueous phase is extracted twice with DCM (2×100 ml). The organic phases are collected, dried ($MgSO_4$) and the DCM is evaporated to yield a thick syrup. The α/β ratio can be seen from HPLC but there is no really difference in Rf (MeOH/DCM: 5:95) compared to the starting material. The TLC is developed in 20% Sulphuric acid+heat.

This product is used without further purification.

EXAMPLE 3

1-(2-O-acetyl-3-O-benzyl-4-C-methanesulfonyloxymethyl-5-O-methanesulfonyl-β-D-ribofuranosyl)-2-amino-6-chloro purine (4)

N,O-bis(trimethylsilyl)acetamide (29.6 g, 35 ml) was added to a stirred slurry of (3) (30 g, 58.8 mmol) and 2-amino-6-chloropurine (12 g, 70 mmol) in 1,2-dichloroethane (dried over sieves, 450 ml) and the mixture was refluxed for 40 min. to give a homogenous solution. The mixture was then removed from the heat and trimethylsilyltriflat (22 ml, 118 mmol) was added dropwise. The reaction mixture was refluxed for another 2 h. The reaction mixture was cooled to room temperature and a saturated aqueous solution of bicarbonate (400 ml) was added. The slurry was allowed to stir for 15 min, pH was adjusted to 7–8 using glacial acetic acid and the mixture was extracted with chloroform. The aqueous phase was extracted with AcOEt and chloroform and the organic phases were combined. The organic phase was washed with brine (2×250 ml) and bicarbonate (2×250 ml). The organic phase was dried over sodium sulfate and concentrated under reduced pressure to give compound (4) as a yellowish foam which expands during vacuum dessication Yield: 35.4 g, 97%.

EXAMPLE 4

(1S,3R,4R,7S)-7-Benzyloxy-1-methanesulfonyloxymethyl-3-(guanine-9-yl)-2,5-dioxabicyclo[2:2:1]heptane (5)

A solution of 3-hydroxypropionitrile (22.6 g, 21.7 ml) in dry THF (75 ml) was added over 15 min to a stirred suspension of sodium hydride (14 g, 60% suspended in mineral oil) in dry THF (250 ml) and the mixture was stirred for 30 min at ambient temperature.

1-(2-O-acetyl-3-O-benzyl-4-C-methanesulfonyloxymethyl-5-O-methanesulfonyl-β-D-ribofuranosyl)-2-amino-6-chloropurine (4) (35.4 g, 57 mmol) dissolved in dry THF (300 ml) was added dropwise in 10 min. and the reaction mixture was stirred until HPLC showed total conversion of 4 to 5, additionally 30 min. Water (600 ml) was added to the reaction mixture and pH was adjusted to 7–8 using glacial acetic acid. The resulting slurry was subsequently extracted with EtOAc (4×300 ml) and the organic phases were combined. The organic phase was dried over sodium sulphate and concentrated under reduced pressure. The resulting oil was successively treated with MeOH and heated to reflux under vigorous stirring to afford a slurry which after hot-filtering afforded compound (5) light-yellow crystals (16 g). A final evaporation of the mother liquor yielded another 8 g as a crude brownish solid.

Combined yield: 90%

EXAMPLE 5

(1S,3R,4R,7S)-7-Benzyloxy-1-methanesulfonyloxymethyl-3-(2-N-isobutyryl-guanine-9-yl)-2,5-dioxabicyclo[2:2:1]heptane (6)

(1S,3R,4R,7S)-7-Benzyloxy-1-methanesulfonyloxymethyl-3-(guanine-9-yl)-2,5-dioxabicyclo[2:2:1]heptane (5) (16 g, 34.6 mmol) is dissolved in DMF (sieves, 200 ml) and isobutyric anhydride (3.5 eq., 20 ml) is added along with N,N-dimethylaminopyridine (0.2 eq., 0.84 g) and the reaction is stirred at 60° C. over night. The volume of the reaction mixture is reduced to 20%, poured into saturated aq. bicarbonate (200 ml) and the mixture is stirred for 30 min. The target molecule is extracted into EtOAc, the organic phase is dried with sodium sulfate and the solvent is removed by evaporation to give compound (6) as a slightly yellow foam (19.9 g), which is used without further purification in the following step.

EXAMPLE 6

(1S,3R,4R,7S)-7-Benzyloxy-1-benzoyloxymethyl-3-(2-N-isobutyrylguanine-9-yl)-2,5-dioxabicyclo[2:2:1]heptane (7)

(1S,3R,4R,7S)-7-Benzyloxy-1-methanesulfonyloxymethyl-3-(2-N-isobutyrylguanine-9-yl)-2,5-dioxabicyclo[2:2:1]heptane (6) (19.9 g from above, approx. 34 mmol) is dissolved in DMF (dried over sieves, 300 ml) and sodiumbenzoate (15 g, 104 mmol, 3 eqv.) is added along with catalytic amounts of cesiumcarbonate. The mixture is heated to 90° C. and allowed to react over night. The solution is filtered and EtOAc is added to the filtrate to precipitate sodiumbenzoate. The mixture is filtered again and washed (water, 2×250 ml), dried ($Na_2SO_4$), and concentrated under reduced pressure to give compound (7) as an oil, which is used without further purification in the following step.

EXAMPLE 7

(1S,3R,4R,7S)-7-Benzyloxy-1-hydroxymethyl-3-(2-N-isobutyrylguanine-9-yl)-2,5-dioxabicyclo[2:2:1]heptane (8)

(1S,3R,4R,7S)-7-Benzyloxy-1-benzoyloxymethyl-3-(2-N-isobutyrylguanine-9-yl)-2,5-dioxabicyclo[2:2:1]heptane (7, 8.2 g, 14.7 mmol) is dissolved in pyridine/ethanol (1:8, 450 ml) and sodium hydroxide (2 M, 15.5 ml) is added. The mixture is allowed to stir for 30 min. at ambient temperature and is subsequently quenched using acetic acid (25 ml). The reaction mixture is concentrated under reduced pressure and the product was crystallised from 20% aqueous ethanol, filtered and dried to give compound (8) (5.8 g, 87%).

EXAMPLE 8

(1S,3R,4R,7S)-7-hydroxy-1-hydroxymethyl-3-(2-N-isobutyrylguanine-9-yl)-2,5-dioxabicyclo[2:2:1]heptane (9)

(1S,3R,4R,7S)-7-Benzyloxy-1-hydroxymethyl-3-(2-N-isobutyrylguanine-9-yl)-2,5-dioxabicyclo[2:2:1]heptane (8)

(5.8 g, 12.7 mmol) is dissolved in methanol (50 ml) and Pd/C (10%, 2 g) was added along with formic acid (3 ml). The mixture was refluxed for 5 h., cooled to ambient temperature and filtrated through silica gel column. The column was washed with methanol (50 ml), all the filtrate was concentrated under reduced pressure to yield compound (9) (4.55 g, 98%) as a glass-like solid.

(1S,3R,4R,7S)-1-(4,4'-Dimethoxytrityloxymethyl)-7-hydroxy-3-(2-N-isobutyryl-guanine-9-yl)-2,5-dioxabicyclo[2:2:1]heptane (10) and (1S,3R,4R,7S)-7-(2-cyanoethoxy (diisopropylamino)phosphinoxy)-1-(4,4'-dimethoxytrityloxymethyl)-3-(2-N-isobutyrylguanine-9-yl)-2,5-dioxabicyclo[2:2:1]heptane (11) are synthesised according to Koshkin et al. (Tetrahedron 54 (1998) 3607–3630.

Examples 9–12 illustrate alternative experimental procedures.

EXAMPLE 9

1,2-O-acetyl-3-O-benzyl-4-C (methanesulfonyloxymethyl)-5-O-methanesulfonyl oxymethyl-)-β-D-ribofuranose (3)

1,2-O-Isopropylidene-3-O-benzyl-4-C-methanesulfonyloxymethyl-5-O-methanesulfonyloxymethyl-β-D-ribofuranose (23.0 g, 49.3 mmol) is suspended at 18° C. under an $N_2$ atmosphere in 82 ml acetic acid (99%) resulting in a light yellow suspension. After 10 minutes of stirring, the substance is still undissolved. Sulphuric acid (98%, 247 mg) dissolved in acetic acid (99%, 2 ml) is thereafter added to the reaction mixture. Clear light yellow solution with white sediment of 1,2-O-Isopropylidene-3-O-benzyl-4-C-methanesulfonyloxymethyl-5-O-methanesulfonyloxymethyl-β-D-ribofuranose. Subsequently, acetic acid anhydrite is added (18° C., 11.2 ml) over 10 minutes without any visible exothermic reaction. The reaction mixture is left over night at room temperature and under inert atmosphere. Clear light yellow solution, with a full conversion of the substrate. 80 ml of tap water is added dropwise to the reaction mixture which is then stirred for 15 minutes at room temperature. 80 ml of acetonitrile is added to the yellow solution which is stirred for another 60 minutes after which the yellow reaction mixture is poured into a separation funnel with good phase separation. The lower unclear organic phase (132 ml) is separated off and the upper blurred aqueous phase (150 ml) containing the product is extracted with further 25 ml methylene chloride. The combined organic phases (110 ml) are washed with 50 ml tap water; pH of the aqueous phase is 2–3. The organic phase is once more extracted with 47 ml tap water; pH of the aqueous phase 2–3. The organic phase is washed two times with 50 ml 1 M $K_2SO_4$. The resulting blurred organic phase is transferred to a round-bottomed flask and is stirred with 25 ml fresh 1M $K_2SO_4$ for 30 minutes after which the clear organic phase is separated in a separation funnel and dried over $MgSO_4$ (6 g). The dried solution is filtrated on a G3 filter, which subsequently is washed with 50 ml methylene chloride. The resulting light yellow solution is evaporated (Rotavapor, 53° C., 100 to 20 mbar). The resulting pale yellow oil is dried intensively (1 mbar, 50° C.). The yield is 27.6 g (102% including residual solvent), and is pure as determined by TLC ($CH_2Cl_2$/TBME/$Et_3N$ 9.5:0.5:0.1); Developer: MeOH/sulphuric acid 1:1.

EXAMPLE 10

1-(2-O-acetyl-3-O-benzyl-4-C-methanesulfonyloxymethyl-5-O-methanesulfonyl-β-D-ribofuranosyl)-2-amino-6-chloro purine (4)

1,2-O-acetyl-3-O-benzyl-4-C (methanesulfonyloxymethyl)-5-O-methanesulfonyl oxymethyl-)-β-D-ribofuranose (3) (25.7 g, 50.4 mmol) is dissolved by gently heating in 242 ml MeCN (HPLC-grade) and is transferred to a 1|3-necked flask with $N_2$-purge, a bubble tube and mechanical stirring. Chloroguanine (9.33 g) is added. BSA (24.5 ml) is added dropwise to the yellow suspension over 5 minutes, 1° C. exothermic temperature increase. The reaction mixture is heated by reflux (80° C.), after which the suspension becomes clear yellow. TMS-OTf (18.2 ml) is added dropwise over 10 minutes via a syringe and under $N_2$. The resulting clear red-orange solution is refluxed for 90 minutes. The reaction mixture is cooled in a water bath to room temperature after which the solution is quenched with 2.5 ml $H_2O$ in 8 ml MeCN, exothermic temperature increase: T=20 to 24° C. 96 ml of tap water is now added to the red solution, no exothermic temperature increase, pH=0.63. 3M NaOH is added dropwise until pH=8. The reaction mixture is shaken with 100 ml water and 120 ml $CH_2Cl_2$. The phases tend to emulsify. Phase-separation: An upper clear yellow aqueous phase and a lower yellow organic phase. The aqueous phase is extracted with 100 ml methylene chloride. The combined organic phases are washed with 100 ml 1M $K_2HPO_4$. The yellow emulsion is filtered on G3 filter and the filter cake (excess chloroguanine) is washed with 20 ml methylene chloride. Volume of upper organic phase: 400 ml; volume of lower aqueous phase 40 ml, pH=6–7. The aqueous phase is washed with 100 ml methylene chloride. The organic phase is washed with 100 ml 1M $K_2HPO_4$; phase separation. The organic phases are combined and further washed with 100 ml 1M $K_2HPO_4$. The phases are separated and yield 620 ml blurred yellow solution which is dried over 26 g $MgSO_4$. After filtering, the clear yellow solution is evaporated (Rotavapor, 53° C., 100 to 1 mbar) to yield 28.7 g (91%) yellow foam. TLC: Only the product can be seen. HPLC: 97% pure.

NOTE: Phase inversion: In spite of a large volume of methylene chloride, the organic phase lies in the top as a yellow phase.

EXAMPLE 11

(1S,3R,4R,7S)-7-Benzyloxy-1-methanesulfonyloxymethyl-3-(guanine-9-yl)-2,5-dioxabicyclo[2:2:1]heptane (5)

3-hydroxypropionitrile (14.84 g, freshly distilled) is dissolved in a 1|3-necked flask with mechanical stirring and $N_2$-flow in THF (257 ml HPLC-grade). The solution is cooled in an ice-bath to less than 5° C., after which 12.2 g (51%) NaH is strewed into the solution in small portions over 10 minutes; slightly exothermic reaction, gas development. The greyish suspension is stirred at 5–10° C. for 30 minutes. 1-(2-O-acetyl-3-O-benzyl-4-C-methanesulfonyloxymethyl-5-O-methanesulfonyl-β-D-ribofuranosyl)-2-amino-6-chloro purine (4) (28.5 g, 46.0 mmol) dissolved in 81 ml dry THF is added dropwise to the reaction mixture over 30 minutes, resulting in a red-brown clear solution which is then stirred at 5° C. for 3 hours. Ion exchanged water (100 ml) is added dropwise (with cooling) over 25 minutes; slightly exothermic reaction, gas development. pH of the reaction mixture is 13. pH is adjusted to pH 7 with 3M HCl (58 ml). The mixture is transferred to a separation funnel. Phase separation (aqueous phase lowest). The aqueous phase is extracted with THF (50 ml). The combined organic phases are extracted twice with NaCl (100 ml, 25%)+$K_2HPO_4$ (25 ml, 1M). pH (resulting aqueous phase) 7. The resulting organic phase (440 ml) is evaporated to near dryness. Re-dissolution in THF (250 ml) and evaporation again. THF (50 ml) is added twice and evaporated to dryness. The remanence is suspended in 146 ml methylene chloride and the suspension is filtrated on G3. Wash with 53 ml methylene chloride. The resulting solution is evaporated to dryness and the remanence is re-dissolved in 145 ml methylene chloride and transferred to a 3-necked flask with 5 ml CH$_2$Cl$_2$. 163 ml TBME is added dropwise and very slowly under vigorous stirring (300 rpm) to the red solution. After addition of 20 ml MTBE, yellow crystals precipitate on the side of the flask. The crystals are scraped into the solution with seed-crystals from the earlier batch. Over 90 minutes, 60 ml of MTBE is added and precipitation is initiated so that a blurred solution is formed. 80 ml added—clear precipitation of light crystals. The solution is seeded again. After 2½ hours all the MTBE is added and the solution is stirred for another 30 minutes. The solution is cooled to 5° C. and filtrated on G3. The yellow filter cake is washed with 100 ml CH$_2$Cl$_2$/MTBE 1:4 and suction dried. The yield is 90.7% (89% pure using HPLC).

Re-precipitation of the raw product: 17.8 g of the filter cake is suspended in 50 ml DMSO in a flask equipped with a mechanical stirrer. The suspension is heated to 90° C. (contact thermometer) and 150 ml of ion exchanged water is slowly added dropwise with a stirring over 30 minutes at 85–90° C. After the addition of 30 ml, a precipitation of a substance on the side of the flask is observed, and after 60 ml precipitation occurs after each drop added. After the last addition, the heating cover is turned off and further 40 ml of water is added. The flask is stirred and allowed to cool to 20° C. Seeding at 50° C. The flask is cooled in an ice-bath to 5° C. and the product is filtrated on a G3 filter. Wash with 2 portions of water (20 ml) and MTBE (30 ml) and dry in a hot-air cabinet. The yield is 15.0 g (66.7%) (94% pure by HPLC).

EXAMPLE 12

(1S,3R,4R,7S)-7-Benzyloxy-1-methanesulfonyloxymethyl-3-(2-N-isobutyryl-guanine-9-yl)-2,5-dioxabicyclo[2:2:1]heptane (6)

(1S,3R,4R,7S)-7-Benzyloxy-1-methanesulfonyloxymethyl-3-(guanine-9-yl)-2,5-dioxabicyclo[2:2:1]heptane (5) (14.0 g, 30.2 mmol) is dissolved in 70 ml pyridine using N$_2$. DMAP (0.50 g) is added. Subsequently, Isobutyric anhydride (16.70 g) is added and the reaction mixture is heated to 60° C. for 4 hours (96% product in the reaction mixture using HPLC). 50 ml of ion exchanged water and 50 ml CH$_2$Cl$_2$ are added to the warm reaction mixture, and the solution is stirred for 60 minutes (in order to quench excess anhydride). 20 ml CH$_2$Cl$_2$ is added and the phases are separated using a separation funnel. The aqueous phase (50 ml) is extracted with 40 ml CH$_2$Cl$_2$. The organic phases are combined and washed with 60 ml ion exchanged water. The phase separation is relieved by using saturated NaCl (5 ml). The clear red organic phase is evaporated (Rotavapor, 50° C., 200 to 10 mbar). The yield is 35.2 g red oil. This oil can be used directly in subsequent steps.

NOTE: The pyridine residual can, if necessary, be removed by azeotropic distillation with toluene.

What is claimed is:
1. A method for the synthesis of purine LNA-analogue having the formula I wherein the two geminal substituents J$^1$ and J$^2$ when taken together represent oxo or thiono, and when taken separately one of them represents OR$^9$, NR$^{10}$R$^{11}$, or SR$^{12}$, and the other together with J$^3$ represents a double bond; when J$^1$ and J$^2$ represent oxo or thiono, J$^3$ represents hydrogen;

W is selected from NR$^1$R$^2$, OR$^3$ and SR$^4$;

A$^1$, A$^2$, A$^3$, and A$^4$ are independently selected from —O—, —S— and —NR$^{13}$—, where R$^{13}$ is selected from hydrogen, optionally substituted C$_{1-6}$-alkyl, optionally substituted C$_{3-6}$-cycloalkyl, optionally substituted (C$_{1-6}$-alkyl)carbonyl and optionally substituted (C$_{3-6}$-cycloalkyl)carbonyl;

each of the substituents R$^1$, R$^2$, R$^3$, and R$^4$ are independently selected from hydrogen, optionally substituted C$_{1-12}$-alkyl, optionally substituted C$_{3-12}$-cycloalkyl, optionally substituted C$_{2-12}$-alkenyl, optionally substituted C$_{2-12}$-alkynyl, optionally substituted aryl, optionally substituted aryl(C$_{1-6}$-alkyl), optionally substituted arylcarbonyl, optionally substituted aryl(C$_{1-6}$alkyl)carbonyl, optionally substituted C$_{1-12}$-alkyl carbonyl, optionally substituted (C$_{3-12}$-cycloalkyl)carbonyl, optionally substituted C$_{2-12}$-alkenyl carbonyl, optionally substituted C$_{2-12}$-alkynyl carbonyl, optionally substituted arylsulfonyl, optionally substituted C$_{1-12}$-alkylsulfonyl, optionally substituted C$_{3-12}$-cycloalkylsulfonyl, optionally substituted C$_{2-12}$-alkenylsulfonyl, optionally substituted C$_{2-12}$-alkynylsulfonyl, optionally substituted C$_{1-12}$-alkoxycarbonyl, formyl, tetrahydropyran-2-yl, optionally substituted heteroaryl, optionally substituted heteroarylcarbonyl, and carbamoyl;

each of the substituents R$^9$, R$^{10}$, R$^{11}$, and R$^{12}$ are independently selected from hydrogen, optionally substituted C$_{1-6}$-alkyl, and optionally substituted aryl;

R$^5$ is selected from optionally substituted alkylsulfonyl, optionally substituted cycloalkylsulfonyl, optionally substituted arylsulfonyl, optionally substituted aryl(C$_{1-6}$alkyl), optionally substituted arylcarbonyl, and tri(alkyl/aryl)silyl;

R$_6$ is selected from optionally substituted aryl(C$_{1-6}$-alkyl), optionally substituted tetrahydropyran-2-yl, optionally substituted arylcarbonyl, optionally substituted aryl, and tri(alkyl/aryl)silyl;

taken together R$^5$ and R$^6$ may also represent di-tert-butylsilylene, 1,3-(1,1,3,3-tetraisopropyl)disiloxanylene or 1,3-(1,1,3,3-tetra-tert-butoxy)disiloxanylene; and n is an integer from 1 to 3;
said method comprising the following step:
treatment of a compound of the formula II:

wherein $A^1, A^2, A^3, A^4, R^5, R^6, R^{13}$, W and n are as defined above;

$A^5$ is selected from —O—, —S— and —NR$^{13}$—;

$R^7$ is selected from optionally substituted alkylsulfonyl, optionally substituted cycloalkylsulfonyl, optionally substituted arylsulfonyl, optionally substituted aryl($C_{1\text{-}6}$alkyl), optionally substituted arylcarbonyl, and tri(alkyl/aryl)silyl;

$R^8$ is selected from hydrogen, optionally substituted ($C_{1\text{-}6}$-alkyl)carbonyl, optionally substituted ($C_{3\text{-}6}$-cycloalkyl)carbonyl, optionally substituted arylcarbonyl, tri(alkyl/aryl)silyl, and fluorenyl($C_{1\text{-}6}$-alkyl)oxycarbonyl; and X is halogen;

with a nucleophilic reagent optionally in deprotonated form, wherein the nucleophilic reagent is $R^9$—OH when $J^1$ and $J^2$ together represent oxo or one of $J^1$ and $J^2$ is $OR^9$ or the nucleophilic reagent is $HNR^{10}R^{11}$ when one of $J^1$ and $J^2$ is $NR^{10}R^{11}$ or the nucleophilic reagent is $R^{12}$—SH when $J^1$ and $J^2$ together represent thiono or one of $J^1$ and $J^2$ is $SR^{12}$, wherein $R^9, R^{10}, R^{11}$ and $R^{12}$ are as defined above.

2. A method according to claim 1, wherein the nucleophilic reagent is 3-hydroxypropionitrile, NH$_3$, 3-mercaptopropionitrile, benzyl alcohol, 2-hydroxyethylbenzene, 2-hydroxy-1-nitroethane and benzylamine.

3. A method according to claim 1, wherein the molar ratio between compound II and the nucleophilic reagent is in the range of 1:2 to 1:10.

4. A method according to claim 3, wherein the molar ratio between compound II and the nucleophilic reagent is in the range of 1:2 to 1:8.

5. A method according to claim 4, wherein the molar ratio between compound II and the nucleophilic reagent is in the range of 1:2 to 1:6.

6. A method according to claim 1, wherein the treatment of compound II with the nucleophilic reagent is performed in the presence of a non-nucleophilic strong base.

7. A method according to claim 6, wherein the treatment of compound II with the nucleophilic reagent is performed in the presence of NaH or LiH.

8. A method according to claim 1, wherein the treatment of compound II with the nucleophilic reagent is performed in the presence of a solvent selected from pyridine, tetrahydrofuran, toluene, xylene, benzene, diethyl ether, acetonitrile, triethylamine, N,N-dimethylformamide, dimethylsulfoxide, dichloromethane and 1,2-dichloroethane.

9. A method according to claim 1, wherein the treatment of compound II with the nucleophilic reagent is performed at −30° C. to 100° C.

10. A method according to claim 1, wherein $A^1, A^2, A^3, A^4$ and $A^5$ all represent oxygen.

11. A method according to claim 1, wherein $R^6$ is selected from benzyl, ortho-, meta-, para-methylbenzyl, 2-chlorobenzyl, 4-phenylbenzyl, tetrahydropyran-2-yl, benzoyl and phenyl.

12. A method according to claim 11, wherein $R^6$ is benzyl.

13. A method according to claim 1, wherein each of the substituents $R^5$ and $R^7$ are selected from methanesulfonyl, trifluoromethanesulfonyl, ethanesulfonyl, 2,2,2-trifluoroethanesulfonyl, propanesulfonyl, iso-propanesulfonyl, butanesulfonyl, nonafluorobutanesulfonyl, pentanesulfonyl, cyclopentanesulfonyl, hexanesulfonyl, cyclohexanesulfonyl, α-toluenesulfonyl, 2-chloro-α-toluenesulfonyl, ortho-, meta-, para-toluenesulfonyl, benzenesulfonyl, ortho-, meta-, para-bromobenzenesulfonyl, ortho-, meta-, para-nitrobenzenesulfonyl, trimethylsilyl, tert-butyldimethylsilyl, and tert-butyldiphenylsilyl.

14. A method according claim 13, wherein each of the substituents $R^5$ and $R^7$ are selected from methanesulfonyl, trifluoromethanesulfonyl, para-toluenesulfonyl and para-bromobenzenesulfonyl.

15. A method according to claim 14, wherein both of the substituents $R^5$ and $R^7$ are methanesulfonyl.

16. A method according to claim 1, wherein $R^8$ is selected from acetyl, benzoyl and m-trifluoromethylbenzoyl.

17. A method according to claim 16, wherein $R^8$ represents acetyl.

18. A method according to claim 1, wherein W represents OH, SH or NH$_2$.

19. A method according to claim 18, wherein W represents NH$_2$.

20. A method according to claim 1, wherein X represents chloro.

21. A method according to claim 1, wherein $A^1, A^2, A^3, A^4$ and $A^5$ all represent oxygen, X is chloro, W is NH$_2$, both of the substituents $R^5$ and $R^7$ are methanesulfonyl, $R^6$ represents benzyl, $R^8$ represent acetyl and n is 1.

22. A method according to claim 1, wherein the compound of the formula II is prepared by coupling of a compound of the formula III:

wherein $A^1, A^2, A^3, A^4, A^5, R^5, R^6, R^7, R^8$ and n are as defined above; and $R^{14}$ is selected from optionally substituted ($C_{1\text{-}6}$-alkyl)carbonyloxy, optionally substituted $C_{1\text{-}6}$-alkoxy, halogen, optionally substituted arylthio, optionally substituted $C_{1\text{-}6}$-alkylthio, and optionally substituted aryloxy;

with a purine of the formula IV:

wherein X and W are as defined above;

in a glycosylation reaction.

23. A method according to claim 22, wherein the glycosylation reaction is performed in the presence of a Lewis acid.

24. A method according to claim 23, wherein the Lewis acid is trimethylsilyl trifluoromethanesulfonate.

25. A method according to claim 22, wherein the glycosylation reaction is performed in the presence of silylating agent.

26. A method according to claim 25, wherein the silylating agent is N,O-bis(trimethylsilyl)acetamide.

27. A method according to claim 22, wherein $R^{14}$ is selected from acetyloxy, methoxy, ethoxy, chloride, fluoride, bromide, iodide, and $SC_6H_5$.

28. A method according to claim 27, wherein $R^{14}$ selected from acetyloxy and methoxy.

29. A compound having the formula I

I wherein one of the two geminal substituents $J^1$ and $J^2$ represents $OR^9$, $NR^{10}R^{11}$, or $SR^{12}$, and the other together with $J^3$ represents a double bond;

W is selected from $NR^1R^2$, $OR^3$ and $SR^4$;

$A^1$, $A^2$, $A^3$, and $A^4$ are independently selected from the group consisting of —O—, —S— and —$NR^{13}$—, where $R^{13}$ is selected from the group consisting of hydrogen, optionally substituted $C_{1-6}$-alkyl, optionally substituted $C_{3-6}$-cycloalkyl, optionally substituted ($C_{1-6}$-alkyl)carbonyl and optionally substituted ($C_{3-6}$-cycloalkyl)carbonyl;

each of the substituents $R^1$, $R^2$, $R^3$, and $R^4$ are independently selected from hydrogen, optionally substituted $C_{1-12}$-alkyl, optionally substituted $C_{3-12}$-cycloalkyl, optionally substituted $C_{2-12}$-alkenyl, optionally substituted $C_{2-12}$-alkynyl, optionally substituted aryl, optionally substituted aryl($C_{1-6}$-alkyl), optionally substituted arylcarbonyl, optionally substituted aryl($C_{1-6}$alkyl)carbonyl, optionally substituted $C_{1-12}$-alkyl carbonyl, optionally substituted ($C_{3-12}$-cycloalkyl)carbonyl, optionally substituted $C_{2-12}$-alkenyl carbonyl, optionally substituted $C_{2-12}$-alkynyl carbonyl, optionally substituted arylsulfonyl, optionally substituted $C_{1-12}$-alkylsulfonyl, optionally substituted $C_{3-12}$-cycloalkylsulfonyl, optionally substituted $C_{2-12}$-alkenylsulfonyl, optionally substituted $C_{2-12}$-alkynylsulfonyl, optionally substituted $C_{1-12}$-alkoxycarbonyl, formyl, tetrahydropyran-2-yl, optionally substituted heteroaryl, optionally substituted heteroarylcarbonyl, and carbamoyl;

each of the substituents $R^9$, $R^{10}$, $R^{11}$, and $R^{12}$ are independently selected from hydrogen, optionally substituted $C_{1-6}$-alkyl, and optionally substituted aryl;

$R^5$ is selected from optionally substituted alkylsulfonyl, optionally substituted cycloalkylsulfonyl, and optionally substituted arylcarbonyl;

$R^6$ is selected from optionally substituted aryl($C_{1-6}$alkyl), optionally substituted tetrahydropyran-2-yl, optionally substituted arylcarbonyl, optionally substituted aryl, and tri(alkyl/aryl)silyl;

taken together $R^5$ and $R^6$ may also represent di-tert-butylsilylene, 1,3-(1,1,3,3-tetraisopropyl) disiloxanylene or 1,3-(1,1,3,3-tetra-tert-butoxy) disiloxanylene; and n is an integer from 1 to 3.

30. A compound according to claim 29, wherein $A^1$, $A^2$, $A^3$, $A^4$ and $A^5$ all represent oxygen.

31. A compound according to claim 29, wherein $R^6$ is selected from benzyl, ortho-, meta-, para-methylbenzyl, 2-chlorobenzyl, 4-phenylbenzyl, tetrahydropyran-2-yl, benzoyl and phenyl.

32. A compound according to claim 31, wherein $R^6$ is benzyl.

33. A compound according to claim 29, wherein $R^5$ is selected from methanesulfonyl, trifluoromethanesulfonyl, ethanesulfonyl, 2,2,2-trifluoroethanesulfonyl, propanesulfonyl, iso-propanesulfonyl, butanesulfonyl, nonafluorobutanesulfonyl, pentanesulfonyl, cyclopentanesulfonyl, hexanesulfonyl, cyclohexanesulfonyl, benzylsulfonyl, 2-chloro benzylsulfonyl, ortho-, meta-, para-toluenesulfonyl, benzenesulfonyl, ortho-, meta-, para-bromobenzenesulfonyl, and ortho-, meta-, para-nitrobenzenesulfonyl.

34. A compound according to claim 33, wherein $R^5$ is selected from methanesulfonyl, trifluoromethanesulfonyl and ortho-, meta-, para-toluenesulfonyl.

35. A compound according to claim 34, wherein $R^5$ is methanesulfonyl.

36. A compound according to claim 29, wherein W represents OH, SH or $NH_2$.

37. A compound according to claim 36, wherein W represents $NH_2$.

38. A compound according to claim 37, wherein $A^1$, $A^2$, $A^3$ and $A^4$ all represent oxygen, W is $NH_2$, $R^5$ is methanesulfonyl, $R^6$ represents benzyl and n is 1.

39. A compound having the formula II:

II wherein W is selected from $NR^1R^2$, $OR^3$ and $SR^4$;

$A^1$, $A^2$, $A^3$, and $A^4$ are independently selected from the group consisting of —O—, —S— and —$NR^{13}$—, where $R^{13}$ is selected from hydrogen, optionally substituted $C_{1-6}$-alkyl, optionally substituted $C_{3-6}$-cycloalkyl, optionally substituted ($C_{1-6}$-alkyl)carbonyl and optionally substituted ($C_{3-6}$-cycloalkyl)carbonyl;

$A^5$ is selected from —O—, —S— and —$NR^{13}$—;

n is an integer from 1 to 3;

each of the substituents $R^1$, $R^2$, $R^3$, and $R^4$ are independently selected from hydrogen, optionally substituted $C_{1-12}$-alkyl, optionally substituted $C_{3-12}$-cycloalkyl, optionally substituted $C_{2-12}$-alkenyl, optionally substituted $C_{2-12}$-alkynyl, optionally substituted aryl, optionally substituted aryl($C_{1-6}$-alkyl), optionally substituted arylcarbonyl, optionally substituted aryl($C_{1-6}$alkyl)carbonyl, optionally substituted $C_{1-12}$-alkyl carbonyl, optionally substituted ($C_{3-12}$-cycloalkyl)carbonyl, optionally substituted $C_{2-12}$-alkenyl carbonyl, optionally substituted $C_{2-12}$-alkynyl carbonyl, optionally substituted arylsulfonyl, optionally substituted $C_{1-12}$-alkylsulfonyl, optionally substituted $C_{3-12}$-cycloalkylsulfonyl, optionally substituted $C_{2-12}$-alkenylsulfonyl, optionally substituted $C_{2-12}$-alkynylsulfonyl, optionally substituted $C_{1-12}$-alkoxycarbonyl, formyl, tetrahydropyran-2-yl, optionally substituted heteroaryl, optionally substituted heteroarylcarbonyl, and carbamoyl;

each of the substituents $R^9$, $R^{10}$, $R^{11}$, and $R^{12}$ are independently selected from hydrogen, optionally substituted $C_{1-6}$-alkyl, and optionally substituted aryl;

$R^{13}$ is selected from hydrogen, optionally substituted $C_{1-6}$-alkyl, optionally substituted $C_{3-6}$-cycloalkyl, optionally substituted $C_{1-6}$-alkyl)carbonyl and optionally substituted ($C_{3-6}$-cycloalkyl)carbonyl;

$R^5$ is selected from optionally substituted alkylsulfonyl, optionally substituted cycloalkylsulfonyl, optionally substituted arylsulfonyl, optionally substituted aryl($C_{1-6}$alkyl), optionally substituted arylcarbonyl, and tri(alkyl/aryl)silyl;

$R^6$ is selected from optionally substituted aryl($C_{1-6}$-alkyl), optionally substituted tetrahydropyran-2-yl, optionally substituted arylcarbonyl, optionally substituted aryl, and tri(alkyl/aryl)silyl;

taken together $R^5$ and $R^6$ may also represent di-tert-butylsilylene, 1,3-(1,1,3,3-tetraisopropyl)disiloxanylene or 1,3-(1,1,3,3-tetra-tert-butoxy)disiloxanylene; and $R^7$ is selected from optionally substituted alkylsulfonyl, optionally substituted cycloalkylsulfonyl, optionally substituted arylsulfonyl, optionally substituted arylcarbonyl, and tri(alkyl/aryl)silyl;

$R^8$ is selected from hydrogen, optionally substituted ($C_{1-6}$-alkyl)carbonyl, optionally substituted ($C_{3-6}$-cycloalkyl)carbonyl, optionally substituted arylcarbonyl, tri(alkyl/aryl)silyl, and fluorenyl($C_{1-6}$-alkyl)oxycarbonyl;

X is halogen.

40. A compound according to claim 39, wherein $A^1$, $A^2$, $A^3$ and $A^4$ all represent oxygen.

41. A compound according to claim 39, wherein $R^6$ is selected from benzyl, ortho-, meta-, and para-methylbenzyl, 2-chlorobenzyl, 4-phenylbenzyl, tetrahydropyran-2-yl, benzoyl and phenyl.

42. A compound according to claim 41, wherein $R^6$ is benzyl.

43. A compound according to claim 39, wherein each of the substituents $R^5$ and $R^7$ independently are selected from methanesulfonyl, trifluoromethanesulfonyl, ethanesulfonyl, 2,2,2-trifluoroethanesulfonyl, propanesulfonyl, isopropanesulfonyl, butanesulfonyl, nonafluorobutanesulfonyl, pentanesulfonyl, cyclopentanesulfonyl, hexanesulfonyl, cyclohexanesulfonyl, α-toluenesulfonyl, 2-chloro-α-toluenesulfonyl, ortho-, meta-, para-toluenesulfonyl, benzenesulfonyl, ortho-, meta-, para-bromobenzenesulfonyl and ortho-, meta-, para-nitrobenzenesulfonyl.

44. A compound according to claim 43, wherein each of the substituents $R^5$ and $R^7$ are methanesulfonyl, trifluoromethanesulfonyl and ortho-, meta-, para-toluenesulfonyl.

45. A compound according to claim 44, wherein both of the substituents $R^5$ and $R^7$ are methanesulfonyl.

46. A compound according to claim 39, wherein $R^8$ represents acetyl, benzoyl and m-trifluoromethylbenzoyl.

47. A compound according to claim 46, wherein $R^8$ represents acetyl.

48. A compound according to any one of claims 39–47, wherein W represents OH, SH or $NH_2$.

49. A compound according to claim 48, wherein W represents $NH_2$.

50. A compound according to claim 39, wherein X represent chloro.

51. A compound according to claim 39, wherein $A^1$, $A^2$, $A^3$, $A^4$ and $A^5$ all represent oxygen, X is chloro, W is $NH_2$, both of the substituents $R^5$ and $R^7$ are methanesulfonyl, $R^8$ represents acetyl and n is 1.

* * * * *